(12) United States Patent
Dordick et al.

(10) Patent No.: US 6,406,668 B1
(45) Date of Patent: Jun. 18, 2002

(54) SENSING ARRAY AND SENSOR STRUCTURE

(75) Inventors: Jonathan S. Dordick, Schenectady; Jungbae Kim; Xiaoqiu Wu, both of Troy, all of NY (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/227,269

(22) Filed: Jan. 8, 1999

Related U.S. Application Data

(60) Provisional application No. 60/095,111, filed on Aug. 3, 1998.

(51) Int. Cl.[7] .............................................. G01N 21/64
(52) U.S. Cl. ................................ 422/82.07; 422/82.08; 436/172
(58) Field of Search ........................... 422/82.05, 82.07, 422/82.08; 436/172

(56) References Cited

U.S. PATENT DOCUMENTS

| | | | |
|---|---|---|---|
| 4,194,877 A | * 3/1980 | Peterson | 436/163 |
| 4,580,059 A | 4/1986 | Wolfbeis et al. | 250/459 |
| 5,019,350 A | * 5/1991 | Rhum et al. | 204/431 |
| 5,102,625 A | 4/1992 | Milo | 422/82.07 |
| 5,244,813 A | 9/1993 | Walt et al. | 436/172 |
| 5,250,264 A | 10/1993 | Walt et al. | 422/82.07 |
| 5,266,271 A | 11/1993 | Bankert et al. | 422/82.07 |
| 5,336,714 A | 8/1994 | Krutak et al. | 524/608 |
| 5,354,825 A | * 10/1994 | Klainer et al. | 250/461.1 |
| 5,405,975 A | 4/1995 | Kuhn et al. | 549/347 |
| 5,442,045 A | 8/1995 | Haugland et al. | 530/391.3 |
| 5,480,723 A | * 1/1996 | Klainer et al. | 428/441 |
| 5,514,748 A | 5/1996 | Isutsumi et al. | 524/600 |
| 5,545,517 A | 8/1996 | Thompson et al. | 435/4 |
| 5,646,863 A | 7/1997 | Morton | 364/496 |
| 5,676,820 A | 10/1997 | Wang et al. | 205/777.5 |
| 5,700,897 A | * 12/1997 | Klainer et al. | 528/15 |
| 6,239,248 B1 | * 5/2001 | Gerber | 528/129 |
| 6,294,390 B1 | * 9/2001 | Barnard et al. | 436/164 |

* cited by examiner

Primary Examiner—Jeffrey Snay
(74) Attorney, Agent, or Firm—Woodard, Emhardt, Naughton Moriarty & McNett

(57) ABSTRACT

A sensor and sensing array are disclosed. These devices include one or more fluorescent polymers selected to register one or more analytes. These analytes may include various metal ions or volatile organic compounds. The sensor and sensing array are responsive to excitation light to emit fluorescence responses indicative of the analytes. In particular, the sensing array may provide a pattern of responses operable as a "chemical nose" to identify one or more of the analytes. Techniques for using and making the sensor and sensing array are also disclosed.

20 Claims, 7 Drawing Sheets

SENSING ARRAY AND SENSOR STRUCTURE

CROSS-REFERENCE TO RELATED APPLICATIONS

The present application claims the benefit of U.S. Provisional Application Ser. No. 60/095,111, filed on Aug. 3, 1998.

GOVERNMENT RIGHTS

The U.S. Government has a paid-up license in this invention and the right in limited circumstances to require the patent owner to license others on reasonable terms as provided for by the terms Contract No. N000149710552 awarded by the United States Navy.

FIELD OF THE INVENTION

This invention relates to a fluorescent sensor and sensing array. More specifically, but not exclusively, this invention relates to a sensor with a fluorescent polyphenol based composition comprising phenolic repeating units and fluorophore units, a sensing array including one or more such sensors, and a method of detecting metal-ions and volatile organic molecules with such sensors.

BACKGROUND OF THE INVENTION

The presence of metal ions and organic compounds in water and the atmosphere results from natural causes or from manmade activities. The ability to detect, identify, and quantify these analytes is of extreme importance for environmental monitoring, remediation efforts, process control, and public safety. Specifically, the ability to analyze organic compounds in low concentrations is required to monitor manufacturing processes, locate and identify hazardous chemicals, and detect regulated substances. Detection of metal ions is needed for identification of hazardous materials, metallic objects and even explosive devices, such as mines.

Currently, there are sensors that exhibit high sensitivity and selectively; however, these sensors are often analyte-specific in that they can detect very low concentrations of a single analyte. In actual practice, it is rare that an analyte will be present to the exclusion of other analytes. Thus, it is highly desirable to provide a sensor that can detect, identify and quantify individual analytes in the presence of a wide variety of analogous species. Often, analyte-specific sensors cannot be practically used to analyze a given analyte mixture. Furthermore, mixtures of analytes frequently inhibit the selectivity and sensitivity of such analyte-specific sensors.

An alternative to using highly sensitive and uniquely selective sensors is to use an array of moderately sensitive sensor elements that respond to a given analyte or a mixture of analytes by providing a unique response or fingerprint that can be correlated to the concentration and identity of each analyte in the mixture. Recognition of this fingerprint mimics natural responses. While nature has provided some species such as dogs with highly sensitive and selective sensory elements or olfactory devices (i.e., noses) that can effectively analyze a mixture of analytes, analytical chemists have only recently been successful in developing a "chemical nose." At the most fundamental level, chemical noses mimic nature's ability to accurately and sensitively detect and identify chemical agents that are present either in solution or the vapor phase. Patterns of responses based upon the individual analytes in the mixture are processed to provide a fingerprint for any given analyte and its concentration, even in the presence of a complex mixture of analytes.

SUMMARY OF THE INVENTION

There is provided in accordance with one form of the present invention a fluorescent sensor comprising a fluorescent polymer composition that is suitable for detecting one or more analytes. The fluorescent polymer composition comprises phenolic repeating units and one or more fluorophore units. These units may associate with a given analyte or analytes to form sensor-analyte complexes. An emission source is included to stimulate a fluorescence response of the composition and a detector registers this response. Irradiation of the composition-analyte complex(es) with the emission source causes the fluorescent components of the complex to fluoresce in a different way from the components without analytes. The fluorescence response is indicative of the analyte or mixture of analytes as measured with the detector.

In another form, a number of different fluorescent materials are provided to form a sensing array. One or more of these materials may be a polymer having a number of phenolic repeating units. These materials may each be one of a number of polymers differing from one another in any of a number of characteristics including the type and degree to which fluorophore units are incorporated, the identity of the phenolic repeating units, and the length of the polymer chain to name a few. Exposure of the sensing array to a single analyte in its environment or a multiple of analytes provides a fluorescent response or a pattern of responses that can be correlated to the identity and concentration of analyte(s) in the mixture.

A further form of the present invention includes: (a) placing a sensor in contact an analyte in solution that includes a polymer having a plurality of phenolic repeating units and at least one fluorophore unit distinct from the phenolic repeating units; (b) irradiating the polymer during contact with the solution to generate a fluorescence response from the polymer; and (c) detecting the fluorescence response corresponding to the analyte.

There is also provided in accordance with still another form of the present invention a method of preparing a fluorescent polymer by co-polymerization of phenol and fluorophore monomers or oligomers. The polymerization can be performed using a variety of polymerization techniques and reaction conditions including chemical polymerization, enzyme catalyzed polymerization, and solid phase synthesis. Use of enzyme catalyzed polymerization or solid phase synthesis provides a high degree of control over the polymerization reaction to provide unique polymers or oligomers having a predetermined sequence of monomeric units, degree of polymerization (DP), and degree of fluorophore incorporation (DI). A wide variety of unique fluorescing polymer compositions may be prepared and bundled together to form a sensor array.

Accordingly, it is one object of the present invention to provide a sensor and sensing array to detect one or more analytes based on fluorescence.

It is an additional object to provide a method of operating such sensors and arrays.

It is another object to provide a fluorescent polymer having phenolic repeating units and one or more fluorophore units useful in sensing various analytes.

It is still another object to provide a process to prepare fluorescent polymers from phenol and fluorophore monomers.

Further objects, features, aspects, forms, advantages and benefits of the present invention shall become apparent from the description and drawings contained herein.

DESCRIPTION OF THE PREFERRED EMBODIMENTS

Figure 1:
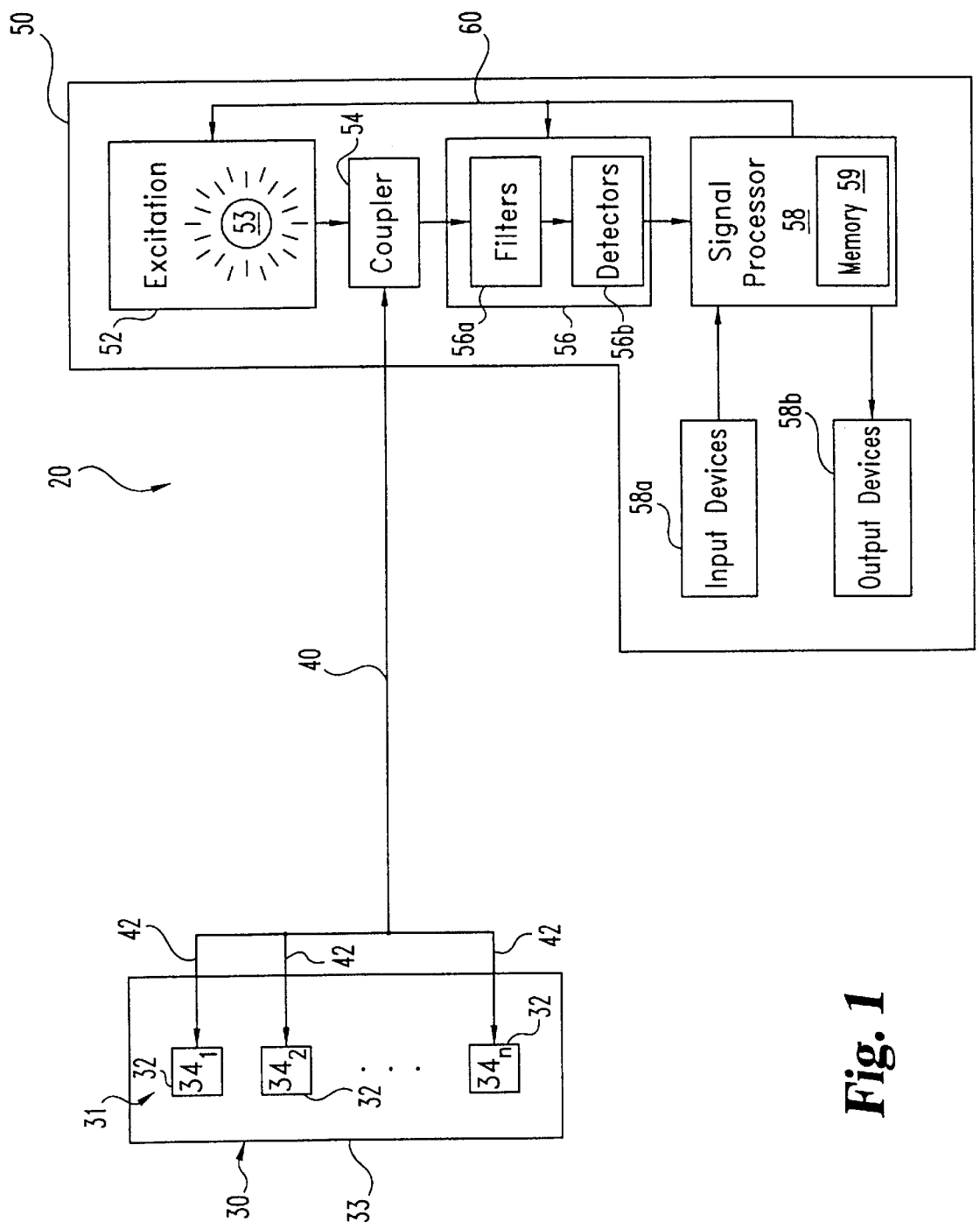
FIG. 1 is a diagrammatic view of a sensing system of the present invention.
Figure 2:
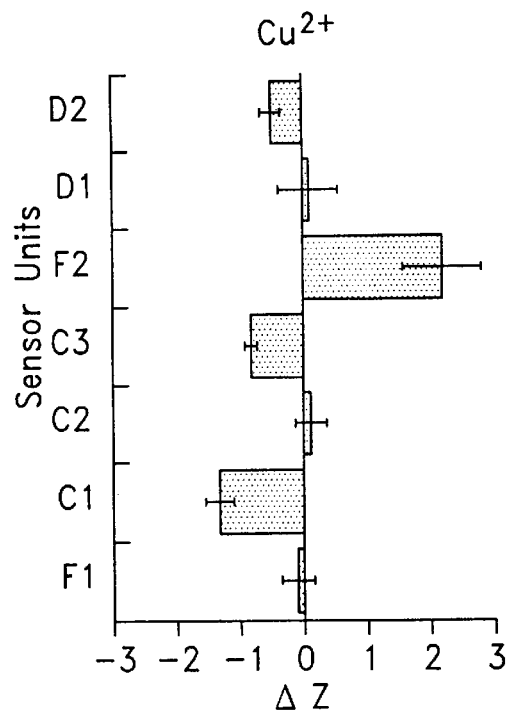
FIGS. 2–6 are histograms depicting the fluorescence response of a polyphenol based sensor array for $Cu^{2+}$, $Fe^{2+}$, $Zn^{2+}$, $Mn^{2+}$, and $Fe^{3+}$ metal ions, respectively.
Figure 3:
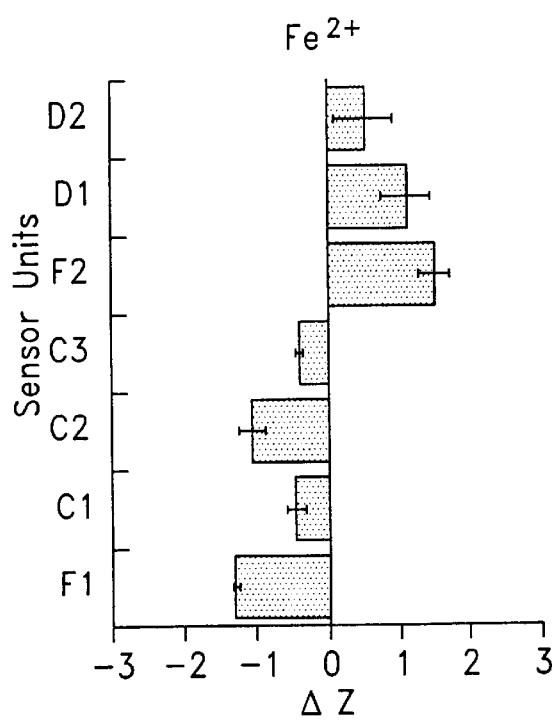
Figure 4:
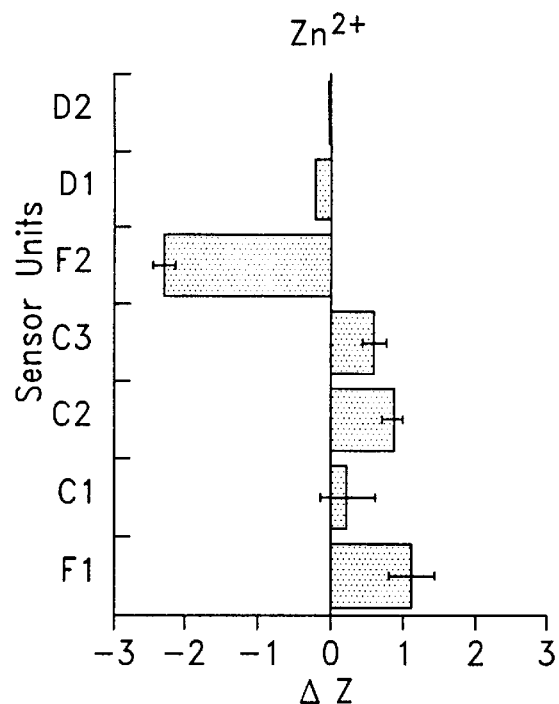
Figure 5:
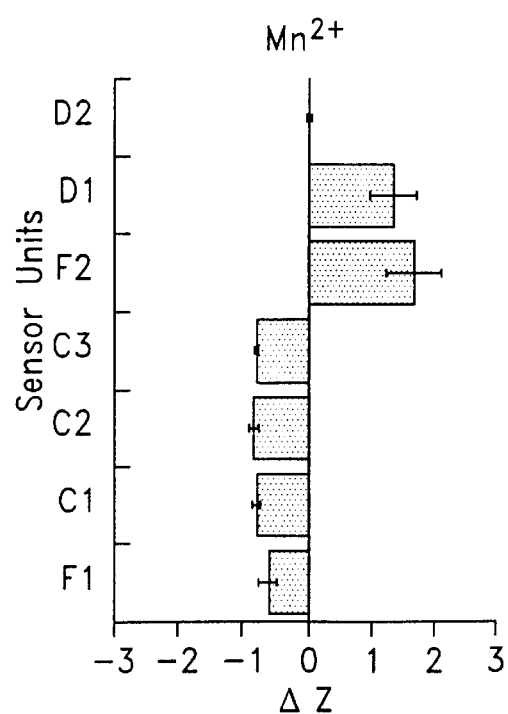
Figure 6:
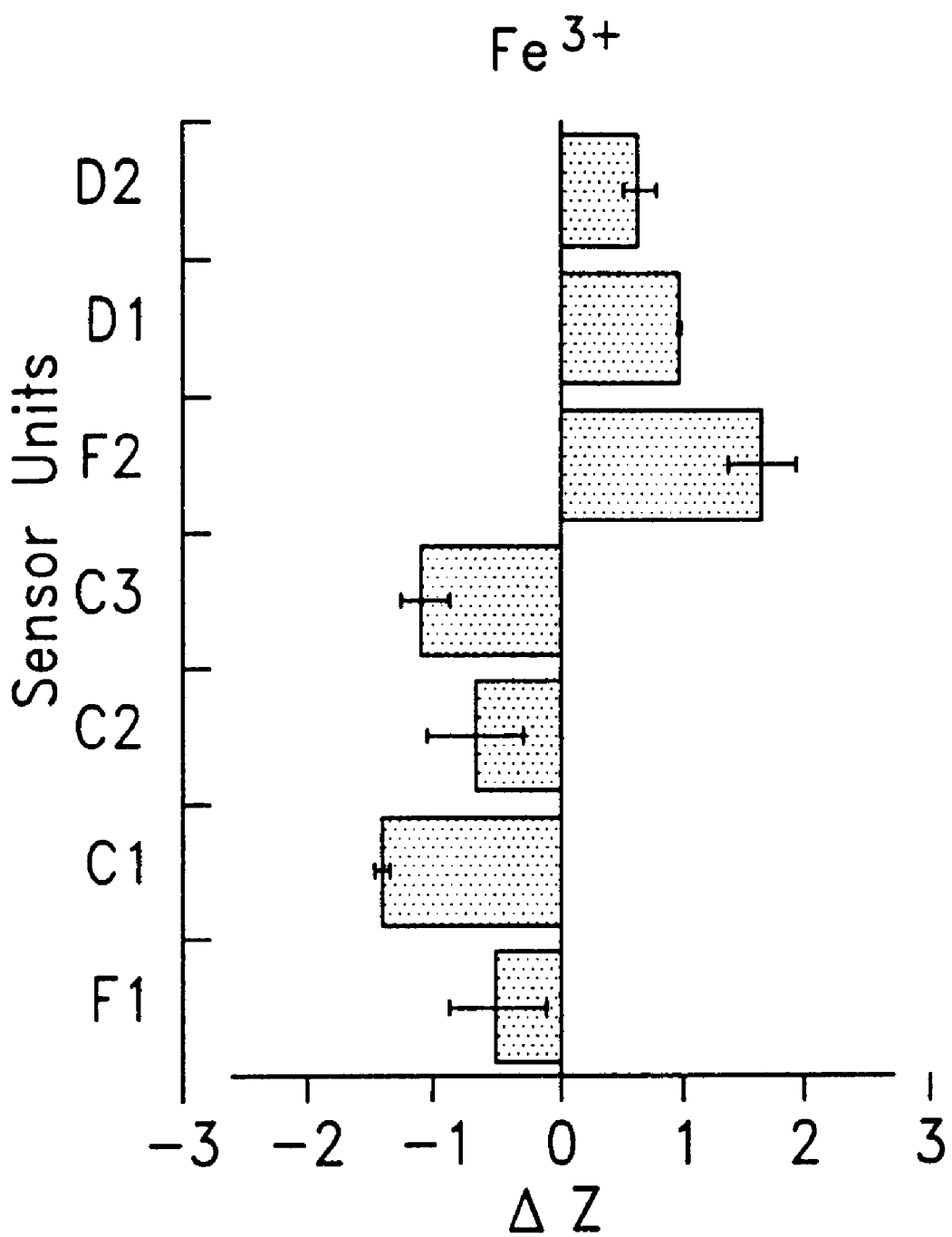

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

Generally this invention relates to fluorescent sensors useful either singly or as a combination of two or more sensors in a sensor array. Under appropriate conditions, the sensors each provide a fluorescence response to an excitation light that is indicative of one or more analytes of interest. By exposing several sensors each having a fluorescent material that responds differently to a common sample, additional information about the analyte(s) may be obtained.

FIG. 1 diagrammatically depicts sensing system 20 of the present invention to analyze fluids, such as liquid solutions and gases, containing various analytes. System 20 includes sensing probe 30 configured to contact fluids containing one or more analytes of interest. Fiber optic cable 40 operatively couples probe 30 to analysis station 50. Preferably, system 20 is configured to remotely locate probe 30 relative to station 50 via cable 40. In one preferred embodiment, probe 30 is positioned in a body of water, such as a stream, river, lake, sea, or ocean, that is to undergo analysis.

Sensing array 31 has "n" number of sensors 32 mounted on support 33. Support 33 may be a substrate or in such other form as would occur to those skilled in the art. As depicted, sensors 32 are generally arranged along a straight axis; however, any other arrangements may be utilized as would occur to those skilled in the art. U.S. Pat. No. 4,580,059 to Wolfbeis et al. is provided as an additional source of information concerning various multiple sensor structures for fluorometric assessment of samples and is hereby incorporated by reference.

Sensors 32 each include a different fluorescent sensing material or matrix. These different materials are individually designated in FIG. 1 by the reference numerals $34_1$, $34_2$, . . . , $34_n$ indexed to the integer "n" (generally designated fluorescent materials 34). The depicted ellipsis represents sensors 32 and the different fluorescent materials 34 necessary to provide the "n" number.

Preferably, Fluorescent materials 34 are selected to facilitate operation of system 20 as a "chemical nose" device for analyzing one or more corresponding analytes in solution. It is also preferred that one or more of fluorescent materials 34 be provided as different phenolic-based polymers or oligomers. Phenol monomeric units of this polymer or oligomer may include a wide variety of pendant functional groups so long as these groups do not prevent detection of one or desired analytes. It is understood for the purposes of this invention that the terms phenol and phenolic refer broadly to a class of aromatic compounds having a hydroxyl group directly attached to the aromatic ring. The phenol-based polymer or oligomer can be a homopolymer, copolymer or terpolymer. Thus, for example, the phenol-based polymer can be comprised exclusively of identical phenol monomeric units such as p-cresol to provide a homopolymer or, alternatively, the phenol-based polymer can comprise two different phenols such as p-cresol and p-methoxyphenol to provide a copolymer. Similarly, a terpolymer comprising three or more phenols can be prepared in accordance with the present invention. The copolymer and terpolymer can comprise uniformly repeating or randomly inserted monomers, block copolymeric, block terpolymeric or block oligomeric units. The polymer may have a variable chain length in that the degree of polymerization (DP) is preferably from about 5 to greater than about 150. Furthermore, the polymeric composition can include cross-linked polymeric chains to provide a polymeric matrix that can incorporate fluorescent components, which also can be polymers or oligomers.

One preferred embodiment of the fluorescent polymer compositions of the present invention includes phenolic repeating units and fluorophore units different from the phenolic units. For this embodiment, phenolic repeating units may be in accordance with formula (1) as follows:

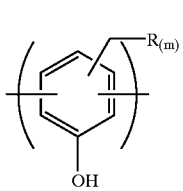

(1)

where, "m" is an integer with a value in the range of 1 to 3, and "R" may be hydrogen, or a functional group substituted for hydrogen on the aromatic ring such as: hydroxyl, halogens, $C_1$ to $C_{10}$ alkyl, $C_1$ to $C_{10}$ alkenyl, $C_1$ to $C_{10}$ alkynyl, $C_1$ to $C_{10}$ alkoxy, $C_1$ to $C_{10}$ mono- and di-alkyl amino, $C_1$ to $C_{10}$ mono- and di-alkanolamino, aryl, $C_1$ to $C_{10}$ alkylaryl, $C_1$–$C_{10}$ alkoxyaryl, $C_1$ to $C_{10}$ alkoxycarbonyl, carboxy, and $C_1$ through $C_{10}$ alkoxycarbonylamino. In addition, biologically active phenols such as tyrosine and tyrosine dipeptides or oligomers are suitable for use in the present invention. Of course, unsubstituted phenol is also included in the present invention.

Specific examples of preferred phenolic repeating units of the present invention include but are not limited to pyrocatechol, resorcinol, hydroquinone 4-chlorophenol, 4-bromophenol, 4-iodophenol, 3,4-dichlorophenol, 2,6-dichlorophenol, 2,5-dichlorophenol, and 2,4-dichlorophenol. Examples of alkyl phenols that are useful in the present invention include p-cresol, 4-ethylphenol, 3-ethylphenol, 4-propylphenol, 3-propylphenol, 4-t-butylphenol, 4-neopentylphenol, 4-isopropylphenol, 4-t-pentylphenol, 4-cyclohexylphenol, 4-cyclopentylphenol, 3,4-dimethylphenol, 3,4-diethylphenol, and 3,5-dimethylphenol. The phenol monomeric units may be substituted with one or more $C_1$ through $C_{10}$ alkoxy substituent groups, for example, 4-methoxyphenol, 3-methoxyphenol, 3,4-dimethoxyphenol, 4-ethoxyphenol, 4-isopropoxyphenol, and 4-octyloxyphenol. One or more aryl functional groups may be included in the phenol unit. Examples include 4-phenylphenol, 3-phenylphenol, bisphenol A and 4,4'-biphenol. The aryl substituent may be in turn substituted with one or more alkyl, alkoxy, halo, amino, nitro, alkylthiol, alkylseleno, alkoxycarbonyl and carboxy substituents. Functional groups also can include mono- and di-alkyl amines; examples of amino functional groups include, methylamine, ethylamine, dimethylamine, and diisopropylamine. In addition to phenolic monomeric units substituted with the above-mentioned functional groups, hydroxy substituted aromatic systems are included in the present invention. Examples include 1-naphthol, 2-naphthol, and phenanthrol. The above list of specific examples is given for illustrative purposes only and is not meant to be limiting in any way.

The preferred fluorophore units incorporated with the phenolic repeating units of formula (1) may be phenol or non-phenol based. It is also preferred that the fluorophore units having a free phenolic or free amino functionality. A few specific, nonlimiting examples of fluorophore units correspond to any of the following: fluorescein, fluorescein, calcein, calcein blue (fluorexon), coumarin, 7-diethylamino-fluoro-methyl coumarin, 3-aminofluoranthene, rosamine, xanthene, rhodamine, substituted xanthylium fluorophores, e.g. fluorescein, 5-isothiocyanate, tetramethylrhodamine-6-isothiocyanate, 5-carboxyfluoroscein, 5-carboxytetramethylrhodamine, rhodamine 101 sulfonyl-chloroide (Texas Red™), 5-carboxy-2',7'-dichlorofluorescein, 5-carboxyseminaphthofluorescein, 5-bromomethylfluorescein, 5-carboxynaphthofluorescein, 5-aminofluorescein, benzoflavine, α-napthylamine, β-napthylamine, salicylic acid, acridine, acridine orange, and β-napthol. The above list of specific examples is given for illustrative purposes only and is not meant to be limiting in any way.

It has been found that fluorophore-fluorophore interactions in these polymers may attenuate the fluorescence of the fluorescent polymer composition. Thus, it is preferred that fluorophore-fluorophore interactions be minimized, if not eliminated, by providing polymeric chains having a low incorporation of the fluorophore units. A preferred range of the degree of incorporation (DI) of fluorophores into the fluorescent polymers of the present invention is about 0.1 to about 10 mole %, more preferably about 0.5 to about 7 mole % based upon the degree of polymerization (DP).

While it is not intended to limit the present invention to any stated theory or mechanism, for this preferred polymer composition of one or more of materials 34, the phenolic repeating units are believed to coordinate to analytes such as metal ions in an aqueous environment and bind to the metal ions. Preferably more than one phenolic hydroxyl groups coordinate to chelate the metal ions to form the sensor-metal complex. This mechanism admits a variety of additional substituents or functional groups. The additional substituents or functional groups modify the physical and chemical characteristics of the polymer. For example, more hydrophobic substituents increase the affinity of Volatile Organic Chemical (VOC) analytes to the fluorescent polymeric composition. The aromatic ring of phenolic units may include up to three functional groups; however, it is more preferred that the two positions on the aromatic ring ortho to the phenolic functional group remain unsubstituted to allow propagation of the polymer chain. It is also more preferred that the functional group(s) not sterically or electronically inhibit coordination or chelation to analytes. Nonetheless, in other embodiments it may be desirable for specific fluorescent polymer compositions to include a phenolic unit having a single position on the aromatic ring that can be bonded to the polymer chain to act as a chain terminating or capping unit. This capping unit may contain up to five substituents or functional groups.

Materials 34 fluoresce when excited or irradiated with radiation at the requisite excitation wavelengths $\lambda_E$. In the case of the preferred polymer compositions having phenolic repeating units and one or more fluorophore units, inclusion of the analyte within the fluorescent polymer composition sterically and/or electronically perturb the physical conformation and electronic environment of the polymer composition. More specifically, the microenvironment around the fluorophore is perturbed, which in turn influences its fluorescence response and the Maximum Emission Wavelength (MEW). A unique fluorescence response and/or MEW is generated based upon the unique perturbations caused by the analyte association with the fluorescent polymer composition. One way to quantitize the fluorescence response of a given one of materials 34 is to provide a spectrum for different analytes in terms of $\Delta F$ as determined from formula (2) as follows:

$$\Delta F = 1 - I/I_0; \tag{2}$$

where, I and $I_0$ are the measured fluorescent emission at the MEW for the polymer-analyte complex and for the free fluorescent polymer, respectively.

While in some instances a single sensor 32 may not provide a sufficiently unique response to a mixture of analytes, a sensing array 31 containing several sensors 32 each having a different fluorescent material 34 provides a correspondingly enhanced fluorescence response pattern useful to analyze the mixture. Each analyte or mixture of analytes provides a unique fluorescence response or pattern of responses when placed in contact with sensor array 31 and exposed to appropriate excitation radiation. The responses are a function of the individual analyte(s) as well as the concentration of the analyte(s). Thus, a sensor array 31 having a plurality of different fluorescent polymer compositions may be used to identify and quantify individual analytes that are components of a complex mixture of analytes.

In one preferred embodiment suitable for metal ion sensing, five sensors 32 are utilized in array 31 (n=5). For this embodiment, the different materials 34 each correspond to different polymers having phenolic repeating units and at least one fluorophore unit. The five materials 34 were: (1) fluorescein-incorporated poly(p-cresol) (designated C1); (2) fluorescence-incorporated poly(p-phenylphenol) (designated C2); (3) fluorescein-incorporated poly(p-methoxyphenol), (designated C3); (4) calcein-incorporated poly(p-cresol) (designated D1); and (5) calcein-incorporated poly(p-phenylphenol) (designated D2). The fluorescence responses of the five sensors 32 to five solutions each containing a single metal ion species are illustrated by the histograms of FIGS. 2–6, respectively. The different respective metal ion analytes are $Cu^{2+}$, $Fe^{2+}$, $Zn^{2+}$, $Mn^{2+}$, and $Fe^{3+}$.

The histograms were developed by calculating the fluorescence changes or statistical deviations (ΔZ) according to formula (3) as follows:

$$\Delta Z = (\Delta F - x)/y; \quad (3)$$

where x and y are the average deviation and the standard deviation of each ΔF value, respectively, over a given metal ion data set. FIGS. 2–6 reveal that the use of multiple, diverse fluorescent materials for each individual metal ion provides a unique fingerprint that can be used as a pattern to recognize the identity and concentration of the analytes in the mixture. Specific examples of metal ions that can be analyzed using the present invention include but are not limited to iron, copper, chromium, manganese, zinc, lead, zirconium, molybdenum, palladium, cadmium, tin, titanium, platinum, gold, silver and mixtures thereof.

Another embodiment suitable for metal ion sensing utilizes eight sensors 32 in array 31 (n=8). For this embodiment, the eight different fluorescent materials 34 are: (1) poly(p-cresol); (2) poly(p-phenylphenol); (3) fluorescein-incorporated poly(p-cresol); (4) fluorescein-incorporated poly(p-phenylphenol); (5) fluorescein-incorporated poly(p-methyoxyphenol); (6) calcein-incorporated poly(p-cresol); (7) calcein-incorporated poly(p-phenylphenol); (8) free calcein or fluorescein.

Returning to FIG. 1, each sensor 32 is operatively coupled to station 50 by optic fiber pair 42 of cable 40, a few of which are depicted. Station 50 includes excitation system 52 and emission detection system 56 connected to fiber optic cable 40 via coupler 54. System 52 includes one or more excitation light sources 53 to provide stimulus to materials 34 of array 31 via cable 40. Sources 53 are preferably monochromatic in nature as may be provided by a laser, Light Emitting Diode (LED), or such other device as would occur to those skilled in the art.

Cable 40 and systems 52, 56 may be variously arranged to accommodate the particular arrangement of sensing array 31. In one embodiment, excitation system 52 has a different source 53 for each of the "n" number of sensors 32. For this embodiment, each pair 42 of cable 40 has a first member that is dedicated to providing excitation light from the corresponding one of sources 53. As a result, a different excitation wavelength may be provided to each of sensors 32, in correspondence with the fluorescent materials 34, as represented by $\lambda_{E1}, \lambda_{E2}, \ldots, \lambda_{En}$ (collectively excitation wavelengths $\lambda_E$); where "n" is the same index as used for materials 34.

For fluorescent materials 34 providing the desired fluorescence in response to the same wavelength (or negligibly different wavelengths), the number of sources 53 may correspondingly be reduced. In one alternative, the same excitation wavelength is used for all fluorescent materials 34 ($\lambda_{E1} = \lambda_{E2} = \ldots = \lambda_{En}$), requiring only one source 53. In another alternative, one or more tunable light sources 53 may be utilized that are time-shared in accordance with a predetermined sequence to provide different excitation wavelengths to corresponding sensors 32. In yet another alternative, one or more sources 53 may provide multiple wavelengths that may be simultaneously sent to one or more of sensors 32. Also, multiple wavelengths from a given source may be separated by filtering (not shown) prior to delivery to sensing array 31 via the corresponding member of pair 42.

In response to the respective excitation wavelengths $\lambda_E$ from the first member of each pair 42, the second member of each pair 42 for a given sensor 32 is provided to transmit a respective fluorescence response. Collectively, the fluorescence responses of sensors 32 correspond to emission wavelengths $\lambda_{F1}, \lambda_{F2}, \ldots, \lambda_{Fn}$ (collectively emission wavelengths $\lambda_F$); where "n" is the same as the index for materials 34 previously described. The fluorescence responses are sent through the second member of each pair 42 of cable 40 to detection system 56 through coupler 54.

Emission detection system 56 is arranged to register the fluorescence response of each sensor 32. System 56 has "n" number of filters to isolate each of the emission wavelengths $\lambda_F$, and a corresponding number of detectors 56b. Each detector 56b may be a photodiode, photomultiplier tube (PMT), or such other type of device as would occur to those skilled in the art. Preferably, there is one detector 56b for each sensor 32; however, in alternative embodiments, fewer detectors may be utilized based on time-sharing in a predetermined sequence as described in connection with system 52.

In other embodiments, the arrangement of cable 40 vary to accommodate the number of sources 53 and detectors 56b. In one alternative, the same source 53 is utilized for each sensor 32, requiring only a single optical fiber for each sensor 32, instead of a pair of optical fibers, plus one optical fiber to deliver the excitation light to all sources; making a total of n+1 fibers in cable 40. In another alternative, it is envisioned that each sensor 32 has a signal optical fiber, instead of a pair, that transmits both the corresponding one of the excitation wavelengths $\lambda_E$ and the emission wavelengths $\lambda_F$, using an optical splitter to couple to both systems 52 and 56. In still other alternatives, sensors 32 may be in a direct proximity to one or more of excitation light sources or emission detectors that correspondingly eliminates the need for an optical cable. Alternatively or additionally, an electrical or wireless connection may be utilized for such arrangements.

For any appropriate arrangement of array 31, cable 40, and systems 52, 56; one or more detection signals are provided by detection system 56 to signal processor 58. Processor 58 is responsive to the detection signals to execute one or more algorithms provided by appropriate hardware and software to gather and analyze relevant data. Processor 58 includes memory 59 to store data and instructions. Processor 58 is also operatively coupled to one or more input devices 58a to receive operator input, and output devices 58b to provide appropriate output to the operator.

In one preferred mode of operation, probe 30 is placed in contact with a solution containing one or more metal ions of interest. The analytes in solution preferably form complexes with one or more of the sensing materials 34 of array 31. Excitation wavelengths $\lambda_E$ are transmitted from system 52 of station 50 via cable 40 to stimulate fluorescence of one or more of sensors 32. Fluorescent responses of sensors 32 are returned to station 50 as one or more emission wavelengths $\lambda_F$ along cable 40 for analysis.

Emission detection system 56 filters and detects intensity of the fluorescence response for each sensor 32 at the corresponding emission wavelengths $\lambda_F$, and provides one or more corresponding detection signals to processor 58. Processor 58 executes appropriate algorithms to determine the ΔF for each sensor 32 of interest based on data for the intensity in the absence of the one or more analytes of interest as stored in memory 59 (See formula (2)). For a given number of sensors n, processor 58 may be configured to establish a detection pattern from the detection signals, ΔF data, or such other fluorescence characteristic information representative of the array 31 responses as would occur to those skilled in the art. The detection pattern may be compared to a one or more known patterns of analyte responses stored in memory 59. Alternatively or additionally, an expert learning system may be utilized through processor 58 to build a library of known analyte patterns using techniques known to those skilled in the art.

One or more output signals may be generated by processor 58 based on the outcome of one or more comparisons or corresponding comparison signals. In response, at least one of output devices 58b outputs data to an operator regarding the qualitative or quantitative aspects of the solution composition. For example, devices 58b may provide an indication such as a print-out or graphical display estimating the metal ions present in the solution and/or the concentration of the metal ions. In other embodiments, VOC analytes may alternatively or additionally be the subject of interrogation by system 20. Systems 52, 56 and processor 58 may be provided by one or more components, units, or pieces of equipment suitable to perform the associated operations. Preferably, systems 52, 56 are configured for electronic communication with and control by processor 58 as represented by control/communication path 60. As used herein, it should be appreciated that: variable, characteristic, emission, criterion, characteristic, comparison, quantity, amount, value, constant, flag, data, record, threshold, limit, input, output, and memory location each generally correspond to one or more signals within systems 52, 56 or processor 58 of the present invention.

Processor 58 may be comprised of digital circuitry, analog circuitry, or both. Also, processor 58 may be programmable, a dedicated state machine, or a hybrid combination of programmable and dedicated hardware. It is preferred that processor 58 include an integrated, solid-state central processing unit operatively coupled to one or more components comprising memory 59. It is also preferred that memory 59 contain programming to be executed by the processing unit and be arranged for reading and writing of data in accordance with the principals of the present invention.

Memory 59 may be comprised of one or more components of the volatile or nonvolatile variety. Further, memory 59 may additionally or alternatively be of the semiconductor, magnetic, or optical type; and may additionally or alternatively include removable media, such as magnetic or optical (CD ROM) disks, or one or more permanently installed memory components. Besides memory 59, it should be understood that processor 58 may also include any control clocks, interfaces, signal conditioners, filters, Analog-to-Digital (A/D) converters, Digital-to-Analog (D/A) converters, communication ports, or other types of components as are known to those skilled in the art; however, these components being generally known, are not shown to enhance clarity of FIG. 1. Similarly, various interfaces, optics, filters, amplifiers, and control elements of systems 52, 56 of a conventional nature may be included as are known to those skilled in the art, but are not shown to preserve clarity.

Input devices 58a may be of a conventional variety such as a keyboard, mouse, voice command subsystem, or such other types as would occur to those skilled in the art. Output devices 58b preferably include a display of the Cathode Ray Tube (CRT) variety and a printer, although other conventional devices may alternatively or additionally be included.

Having described preferred embodiments of the sensors 32 and sensing array 31 of system 20 of the present invention, the operation of system 20, and the preferred phenolic-based polymers utilized as one or more of fluorescent materials 34; preferred processes for preparing such fluorescent materials are next described. Preparation includes polymerization of corresponding phenol monomers. The polymerization can be performed either chemically, enzymatically or via a solid phase synthesis.

Preferably, the phenolic-based polymer compositions are synthesized by an oxidative polymerization using a peroxidase as an enzyme catalyst. The preferable enzyme catalysts include: soybean hull peroxidase (SBP), horseradish peroxidase (HRP), kraft lignin and lignin peroxidase (LiP). The peroxidase catalyzes the 1-electron oxidation of the phenols in the presence of an oxidizing agent such as hydrogen peroxide; provided that other oxidizing agents can also be used. Use of peroxidase catalyzed oxidative polymerization provides greater control of the polymerization reaction, allowing convenient generation of a combinatorial library comprising a large variety of fluorescent polymer compositions for development of an array-based sensor. The peroxidase catalyzes the one electron oxidation of the phenolic monomer upon the addition of an oxidizing agent as shown in formula (4) as follows:

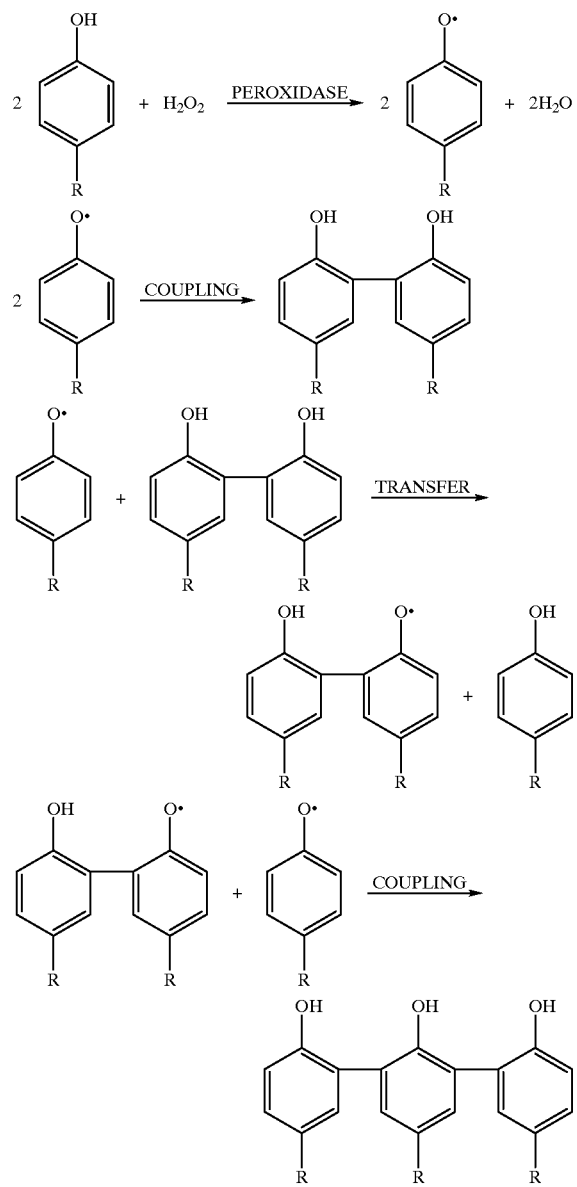

The fluorophores are incorporated into the fluorescent polymer composition in the same manner as the phenol monomers are incorporated into the growing polymer chain. A wide variety of fluorophores act as substrates for the peroxidase catalysts that may be directly incorporated into the growing polymer chain. Preferably, the fluorophore monomers include either a free phenolic or aromatic amine functionality to improve the degree of incorporation in the growing polymer chain.

Co-polymerization of phenols and fluorophores is an effective means for incorporating both monomers into the polymeric background. A reaction mixture can be provided that includes both the phenolic monomer and the fluorophore monomer. Typically, the ratio of phenolic monomer to fluorophore monomer is about 1,000:1 to about 100:1. It is preferred to maintain a low degree of incorporation (DI) of the fluorophore monomer to minimize fluorophore interactions, which generally attenuate the fluorescence of the sensor-analyte complex.

Typically, the peroxidase catalyzed polymerization proceeds at a rapid rate; however, the polymerization can be controlled by the slow addition of an oxidizing agent such as hydrogen peroxide to the reaction mixture. Alternatively, other oxidizing agents such as methyl peroxide, ethyl peroxide and tert-butyl peroxide can be used in place of or in addition to hydrogen peroxide. The reaction is typically carried out in buffered aqueous media. Preferably, the buffered aqueous solution contains a polar organic solvent such as dimethylformamide or dioxane to increase the solubility of the growing polymer chain. The polymeric chain increases in length until it becomes insoluble and precipitates out of solution. The growth of the insoluble polymer is negligible when compared with the rate of polymerization of soluble monomers or oligomers, and the polymerization reaction is essentially quenched upon precipitation.

The insoluble polymer chain can be isolated from the solution. Washing the isolated polymer with copious amounts of aqueous-buffered solution effectively washes away all the unconsumed reactants and catalysts, i.e. phenolic monomers, fluorophore monomers, oxidizing agent, and peroxidase catalyst; to provide a highly pure polymer chain. The polymer chain can be isolated in yields greater than about 70% and have a DP of at least about 5 to about 150. The weight average molecular weight can range from about 400 to greater than 26,000 D. Polymers having a greater DP can be prepared by increasing the amount of organic co-solvent included in the reaction mixture and by varying the functional group(s) attached to the phenolic monomers and fluorophore monomers.

Since the polymerization reaction is essentially stopped upon precipitation of the polymer chain, the DP of the polymer can be controlled by controlling the polymer's solubility. Functional groups on the monomers influence the solubility of the growing polymer chain. More polar groups increase the polymer's solubility in the aqueous buffer solution. Similarly, increasing the amount of organic co-solvent included in the reaction medium also increases the polymer solubility. Thus, the degree of polymerization is controlled by adjusting the organic co-solvent or the judicious selection of the functional group(s) on the monomers or fluorophores.

Alternatively, the fluorescent polymer composition can be prepared by solid phase synthesis. Methods of solid phase synthesis are well-known in the art. Use of solid-phase synthesis provides precise control over the fluorescent polymer composition by providing a method to selectively, sequentially, and controllably add specific monomers to a growing polymer chain. This allows the incorporation of specific monomers at specific sites in the growing polymer chain to control the fluorescent properties of the fluorescent polymer compositions. Finally, this synthetic scheme provides an efficient method to generate a combinatorial library of unique fluorescent polymer compositions.

The solid phase technique requires a synthesis of a support-bound fluorophore material. A functional active solid support is used as a matrix for the synthesis. A fluorophore is chemically attached to the support, and then the peroxidase-catalyzed polyphenol synthesis is carried out. It is understood that a phenol monomer could also be attached to the polymer support in place of the fluorophore monomer. Preferably, poly(hydroxyethylmethacrylate) (pHEMA) is used as the solid support. The cross-linked pHEMA provides a swollen hydrogel that is optically transparent. Thus, fluorescence detection through this support is feasible. Secondly, attachment chemistries are available through a hydroxyl moiety on the polymer that can be chemically activated with a variety of reactants, for example epichlorohydrin, to form a linker group between the pHEMA polymer chain and the fluorophore monomer. The amino or hydroxyl group in many of the fluorophores can be directly attached to the linker group on the pHEMA. An example is shown in formula (5) as follows:

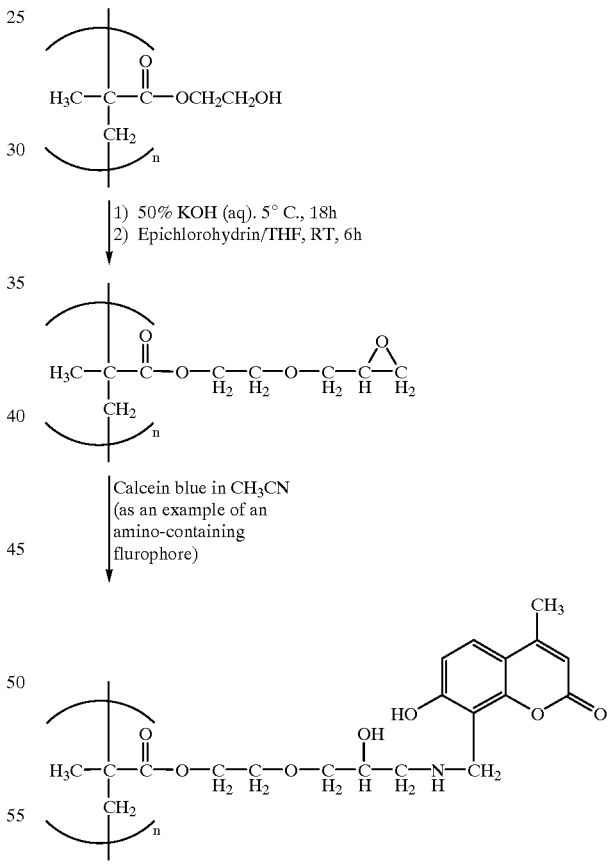

Epichlorohydrin is added to the pHEMA solid support followed by the addition of a fluorophore such as calcein blue to provide the pHEMA-fluorophore complex. The calcium blue contains a free phenolic group that acts as a substrate for the peroxidase catalyzed polymerization. The remaining stepwise addition of phenol monomers is carried out by providing a large excess of the first phenol monomer, a peroxidase enzyme and a sufficient amount of an oxidizing agent to attach the phenolic monomer to the pHEMA-fluorophore complex. The reactants are washed away with copious amounts of water. This sequence is repeated for the second and subsequent steps in the synthesis to provide the stepwise synthesis of a bound fluorescent polymer composition having a predetermined monomer sequence and degree of incorporation. In this fashion, a wide variety of copolymers and terpolymers are synthesized to provide a combinatorial library of unique fluorescent polymer compositions.

Each fluorescent polymer composition in the combinatorial library is screened for use as analyte-sensor. For example, fluorescent polymer compositions are synthesized in an 8×8 array in a 96 well plate. Each well of the plate contains a specific fluorescent polymer composition having a unique and predetermined monomer sequence and DP. An analyte or a solution containing a single or a mixture of analytes is added to each well, and the fluorescent response of the sensor-analyte complex is determined as a function of the identity and concentration of the analyte(s). The fluorescent response from fluorescent polymer in each well of the plate can be determined using a commercially available fluorescence plate reader, such as Perkin Elmer, Model No. HTS 7000 Bio Assay Reader. This procedure can be repeated for a wide variety of metals or VOCs. For example, an aqueous solution of $Cu^{2+}$ ions provides a spectrum of fluorescence responses ($\Delta F$) that are different from that of a solution of $Zn^{2+}$ ions. The fluorescence response $\Delta F$ is calculated using formulae (2) and (3) to obtain histogram spectra comparable to those of FIGS. 2–6.

EXPERIMENTAL SECTION

The following examples are provided for illustrative purposes only and are not intended to be limiting in any manner.

Example 1

Preparation of Poly(p-Cresol) Polymer

The peroxidase-catalyzed polymerization polyphenol synthesis was performed in an aqueous buffer (bis-tris propane buffer, pH 7, 20–33% by volume dimethylformamide). A reaction mixture containing the aqueous buffer, 10 mM of p-cresol and 0.1 mg/ml soybean hull peroxidase (SBP) was prepared. The polymerization reaction was initiated upon the addition of 1M aqueous solution of $H_2O_2$ that was added slowly using a syringe pump to provide a final concentration of 10 mM $H_2O_2$. The reaction mixture quickly formed a precipitate, which was a water insoluble phenolic polymer. The water-insoluble precipitate was washed with excess water to remove unreacted reactants and enzyme.

The p-cresol polymer was isolated in about 75% yield based on the amount of p-cresol consumed. This compares to p-cresol oxidation by horseradish peroxidase (HRP) which resulted in a p-cresol polymer having a weight average molecular weight of 1950 (DP=18).

Example 2

Preparation p-Cresol, Fluorescein Copolymer

Similar to Example 1, the peroxidase-catalyzed polymerization reaction was performed in aqueous buffer (bis-tris propane buffer, pH 7, 20–33% by volume dimethylformamide) containing 10 mM of p-cresol, 1 mM of fluorescein, and 0.1 mg/ml SBP. The reaction was initiated upon the addition of a 1 M aqueous solution of $H_2O_2$ that was slowly added using a syringe pump to provide a final concentration of 10 mM $H_2O_2$. The polymer quickly precipitated from the reaction. The precipitate was isolated and washed extensively with water to yield a yellowish powder. Washing the powder with copious amounts of water removed unreacted fluorescein and baseline fluorescence measured with optimum excitation and emission wavelengths of 496 and 511.6 nm, respectively. The soybean hull peroxidase (SBP) catalyzed the nearly complete oxidation of p-cresol over a period of about 4 hours with the rate of conversion controlled by the slow addition of $H_2O_2$ into the reaction mixture. (See FIG. 7). The progress of the peroxidase-catalyzed phenolic polymerization was monitored by HPLC using a $\mu$-Bondapak $C_{18}$ column (3.9×300 mm) from Waters (Franklin Mass.) with a mobile phase of 40% acetonitrile in HPLC-grade water. Detection was achieved at 277 nm for p-cresol and at 490 nm for free fluorescein. Aliquots for HPLC analysis were prepared by ultrafiltering (300 MWCO) the reactant supernatant after quenching reaction with concentrated citric acid solution.

Figure 7:
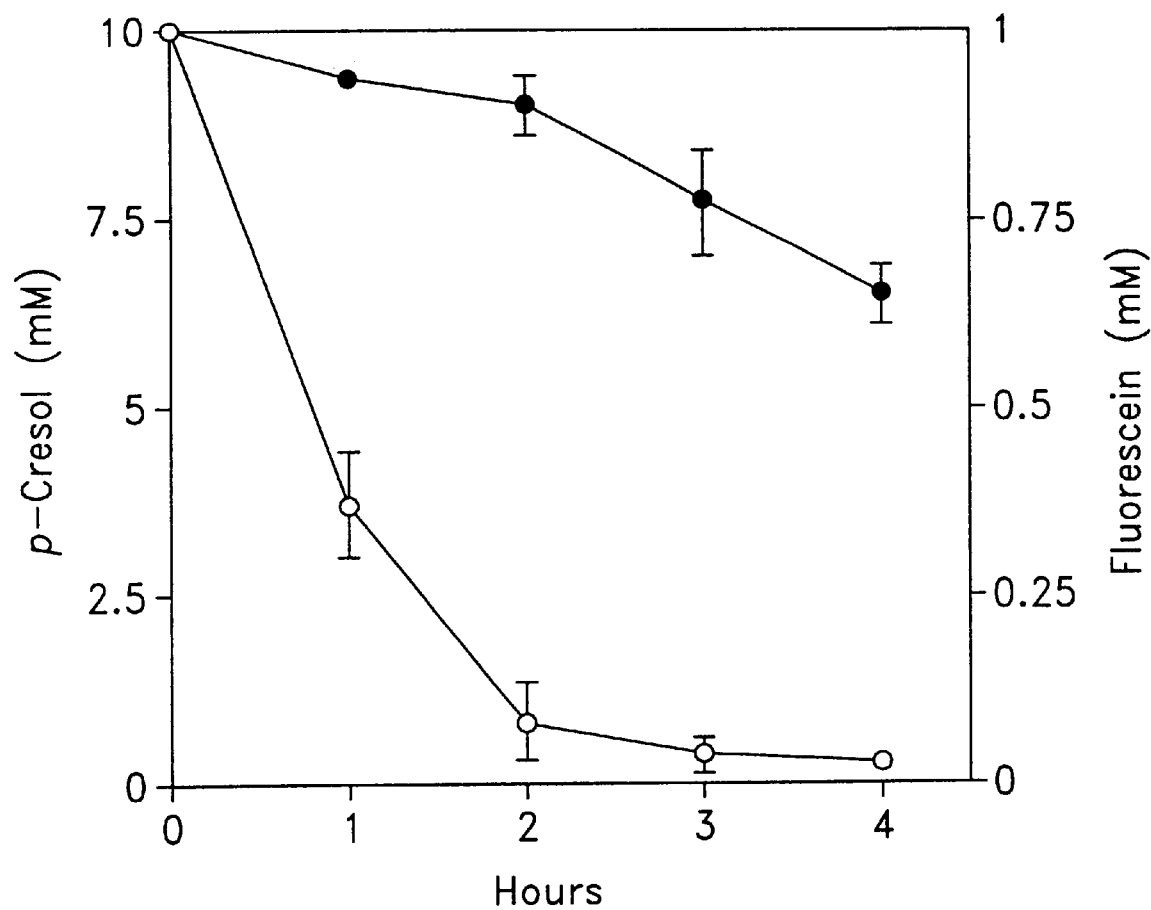
FIG. 7 is a graphical illustration of the consumption of p-cresol and fluorescein during enzyme catalyzed polymerization.

From the results graphically displayed in FIG. 7, it was concluded that about 10 mM of p-cresol reacted with per 0.3 mM of fluorescein. Thus, the degree of incorporation of fluorescein into the polymer was no greater then about 3 molar %. Given the average molecular of about 1950 (DP=18), about one fluorescein monomer was incorporated into every other polymer chain.

To ensure that no polyfluorescein contributed to the observed fluorescence, an analogous SBP-catalyzed oxidation of fluorescein in the absence of a phenol was performed. Although the fluorescein was oxidized (as determined by HPLC data) no precipitate formed, indicating that only low molecular weight oligomers were produced. Importantly, such homopolymers or oligomers of fluorescein would be washed away with the unreacted fluorescein and would not contribute to the observed fluorescence of the copolymers prepared from phenol and fluorophore units.

Example 3

Preparation of Polyphenol-based Polymers

The procedures described in Examples 1 and 2 were determined to be of general utility and were used to prepare a variety of flourescent polymer compositions including poly(p-cresol), poly(p-cresol-co-fluorescein), poly(p-cresol-co-casein), poly(p-phenyl phenol), poly((p-phenyl phenol)-co-fluorescein), poly((p-phenyl phenol)-co-casein), poly(p-methoxyphenol), poly(p-methoxyphenol-co-fluorescein) and poly(p-methoxyphenol-co-casein).

Example 4

Solid-Phase Synthesis of Polyphenol-based Metal Ion Sensor

Fluorescein is chemically attached to a solid support, such as poly(hydroxyethylmethacrylate) (pHEMA). The solid support is suspended in an aqueous buffer solution comprising excess phenol such as p-cresol and a peroxidase such as HRP or SBP and the polymerization is initiated by the slow addition of a 1 M solution of $H_2O_2$ via a syringe pump to give a final concentration of about 10 mM $H_2O_2$. The reaction is monitored as described in Example 2 to ensure the desired chain length is achieved. The polymerization reaction is quenched by adding citric acid. Then the solid support including the bound fluorescent polymer is separated from the aqueous buffer solution.

Example 5

Solid-Phase Synthesis of Terpolymeric Compositions

The solid phase synthesis can be utilized in an analogous procedure to provide terpolymers having a predetermined monomer sequence. Initially, a fluorophore such as fluorescein is chemically bonded to a solid support such as poly (hydroxyethylmethacrylate) (pHEMA) via a linker group provided from epichlorohydrin. A large excess of phenol monomer in an aqueous buffer solution that also includes a peroxidase is combined with the solid phase support including the bound fluorophore. The action was monitored to ensure that a single phenol monomer is added to the polymer support. The excess solution-phase polyphenols are readily separated by washing with an appropriate organic solvent such as DMF to remove nonresin-bound polyphenols. The solid support including the fluorophore and one or more phenol monomers is separated from the solvent The reaction as described above is repeated with a second phenol monomer. The second phenol monomer may be the same or may be different from the previously added phenol monomer. In this fashion, the stepwise addition of specific fluorophore and phenol monomers yields a wide variety of pHEMA bound fluorescent polymer compositions to provide a combinatorial library of unique pHEMA bound fluorescent polymer compounds in a controlled and efficient manner. The combinatorial library can be screened against specific analytes. The bound fluorescent polymer compositions that exhibit the desired activity for the desired metal ions will be removed from the solid support via chemical means, e.g., hydrolysis of the fluorophore from the pHEMA support. The resulting free fluorescent polymeric compositions can be incorporated into a sensor array. For example, the fluorescent composition can be incorporated into a HEMA-based polymer by polyermization of HEMA monomers in the presence of an appropriate radical initiator and the fluorescent polymer composition.

Example 6

Fluorescence Response Determinations for Poly(p-Cresol) and Poly(p-Phenylphenol)

Figure 8:
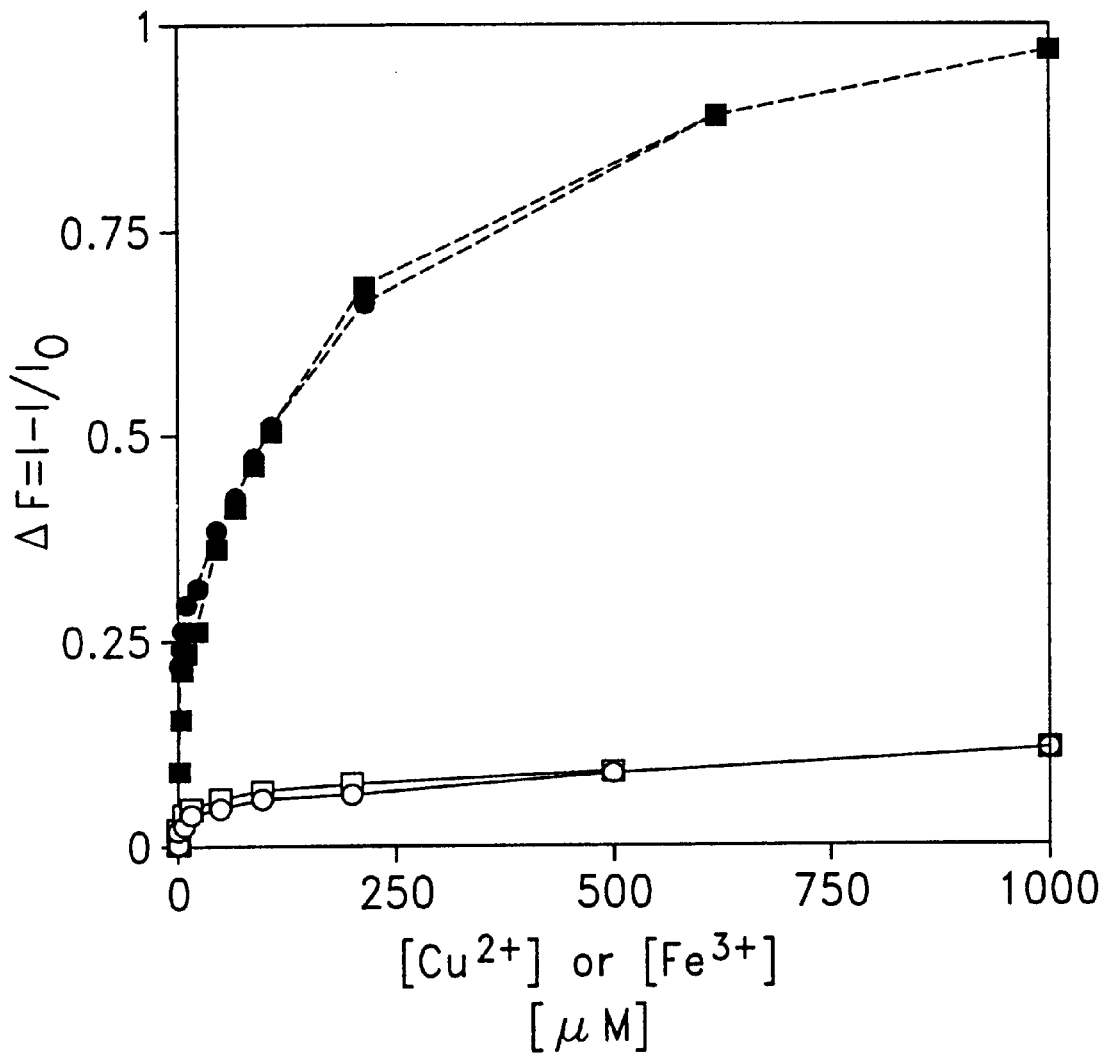
FIG. 8 is a graphical illustration of the fluorescence response of poly(p-cresol) and poly(p-phenylphenol) to $Cu^{2+}$ and $Fe^{3+}$ ions.

The poly(p-cresol) and poly(p-phenylphenol) homopolymers were individually suspended in Bis-Tris propane buffer (pH 7.0) solutions that contained either $Ca^{2+}$ or $Fe^{3+}$ metal ions in concentrations ranging from about 1 $\mu m$ to about 1 mM. The suspended polymers were irradiated using a spectrofluorophotometer at an excitation wavelength of 322 nm. The maximal fluorescence excitation I or $I_0$ was recorded at an MEW of 361.6 nm. The results are graphically illustrated in FIG. 8. The fluorescence response $\Delta F$ was calculated according to the following equation: $\Delta F=1-(I/I_0)$, where I and $I_0$ represent the MEW intensities in the presence and in the absence of metal ions, respectively. The fluorescence response $\Delta F$ was calculated from a minimum of 3 independent measurements of I and $I_0$. Both poly(p-cresol) and poly(p-phenylphenol) easily distinguished between the two metal ions, with 1 mM of $Fe^{3+}$ nearly completely quenching the fluorescence. In fact, fluorescence quenching can be obtained in the presence of as little as 10 $\mu m$ $Fe^{3+}$. Thus, the native enzymatically synthesized polymers have inherent metal ion sensitivity. The calculated fluorescence response, $\Delta F$, was used to readily distinguish between the two metals.

Example 7

Determination of Fluorescence Response

Figure 9:
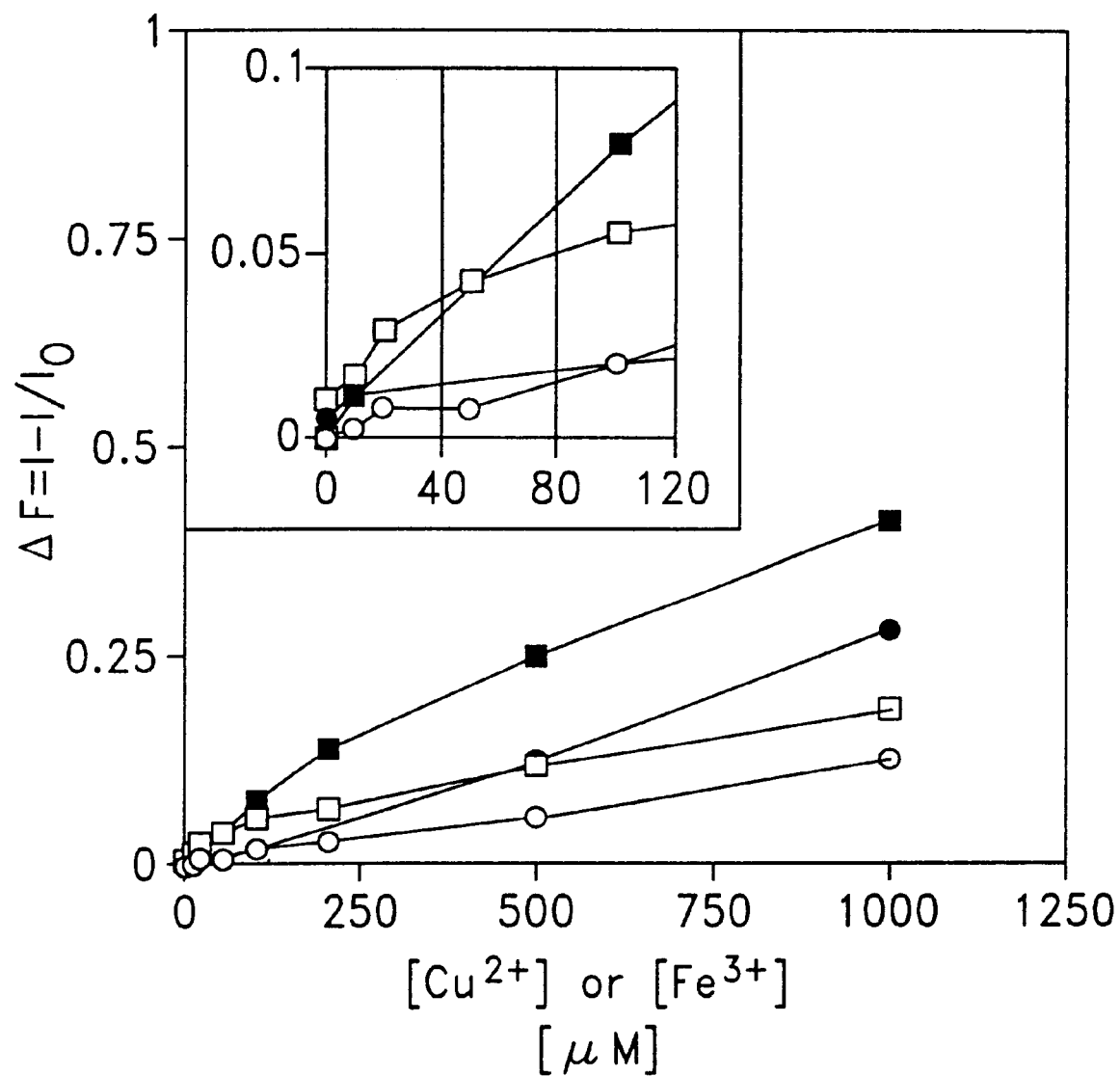
FIG. 9 is graph illustrating the fluorescence response of fluorescein-incorporated poly(p-cresol) and fluorescein-incorporated poly(p-phenylphenol) in the presence of $Cu^{2+}$ and $Fe^{3+}$ metal ions.

Free fluorescein, calcein, and phenolic-based polymers with and without added fluorophore 0.5~50 nm) were individually suspended in a series of solutions containing Bis-Tris propane buffer solution (pH 7.0) and a single metal ion at concentrations ranging from 1 $\mu m$ to 1 mM. After the mixture was sonicated for about 1 minute, the fluorescent intensities at specific maximum emission wave lengths (MEW) were measured with excitation at 322 nm (for polymers without fluorophore), 480 nm (for free calcein and calcein-incorporated polymers) and 496 nm (for free fluorescein and fluorescein-incorporated polymers). (See FIG. 9) The fluorescence response, $\Delta F$, was calculated according to the equation: $\Delta F=1-(I/I_0)$, where I and $I_0$ represent the MEW intensities in the presence and in the absence of metal ions, respectively. The fluorescence response $\Delta F$ was calculated from a minimum of 3 independent measurements of I and $I_0$. The results are listed in Tables 1 and 2.

TABLE 1

|  | $\Delta F\ Cu^{2+}$ | $\Delta F\ Fe^{2+}$ | $\Delta F\ Zn^{2+}$ | $\Delta F\ Mn^{2+}$ | $\Delta F\ Fe^{3+}$ |
|---|---|---|---|---|---|
| Free Fluorescein | 0.18 ± 0.01 | 0.13 ± 0.01 | 0.06 ± 0.02 | 0.05 ± 0.02 | 0.40 ± 0.06 |
| p-cresol, fluorescein copolymer | 0.12 ± 0.001 | 0.33 ± 0.03 | −0.01 ± 0.03 | 0.02 ± 0.01 | 0.26 ± 0.01 |
| p-phenylphenol, fluorescein copolymer | 0.19 ± 0.01 | 0.19 ± 0.04 | 0.04 ± 0.01 | 0.01 ± 0.01 | 0.37 ± 0.06 |
| p-methoxyphenol, fluorescein copolymer | 0.15 ± 0.00 | 0.34 ± 0.01 | 0.02 ± 0.01 | 0.02 ± 0.00 | 0.31 ± 0.04 |

TABLE 2

|  | $\Delta F\ Cu^{2+}$ | $\Delta F\ Fe^{2+}$ | $\Delta F\ Zn^{2+}$ | $\Delta F\ Mn^{2+}$ | $\Delta F\ Fe^{3+}$ |
|---|---|---|---|---|---|
| Free calcein | 0.29 ± 0.03 | 0.79 ± 0.05 | −0.21 ± 0.01 | 0.41 ± 0.07 | 0.75 ± 0.04 |
| p-cresol, calcein co-polymer | 0.19 ± 0.02 | 0.69 ± 0.08 | −0.05 ± 0.00 | 0.36 ± 0.06 | 0.64 ± 0.00 |
| p-phenylphenol, calcein co-polymer | 0.16 ± 0.01 | 0.55 ± 0.10 | −0.03 ± 0.00 | 0.14 ± 0.01 | 0.59 ± 0.02 |

Analysis of the results listed in Tables 1 and 2 indicate that all the fluorescent polymer compositions examined exhibit sensitivity to a wide variety of metal ions in aqueous solution. Under these conditions, polymers poly(p-cresol-co-fluorescein) and poly((p-phenyl phenol)-co-fluorescein) displayed distinct responses from each other for a given metal ion such as $Cu^{2+}$ as well distinct responses for different metals ions such as between $Cu^{2+}$ and $Fe^{2+}$. The $\Delta F$ values for these two copolymers listed in Table 1 are not only distinct but are different from that of free fluorescein, thereby indicating that the fluorescence of this reporter molecule is influenced by a microenvironment of the specific fluorescent polymer composition. The difference in chain size and hydrophobicity between p-cresol's methyl group and p-phenylphenol phenyl group are sufficient to influence the microenvironment in the vicinity of incorporated fluorescein monomers, thereby altering the fluorescence response to different metal ions.

Example 8

Fluorescence Response in the Presence of Two Metal Ions

The fluorescence response of the fluorescent copolymers was examined for a mixture of metals. Poly(p-cresol, fluorescein) copolymer was suspended in a series of solutions containing Bis-Tris propane buffer solution (pH 7.0) and $Cu^{2+}$ and $Fe^{3+}$ both at individually and combined at concentrations ranging from 0.2 mM to 1.0 mM. After the mixture was sonicated for about 1 minute, the fluorescent intensities at specific maximum emission wavelengths (MEW) were measured with excitation at 496 nm. The fluorescence response, $\Delta F$, was calculated according to the equation: $\Delta F=1-(I/I_0)$, where I and $I_0$ represent the MEW intensities in the presence and in the absence of metal ions, respectively. The fluorescence response $\Delta F$ was calculated from a minimum of 3 independent measurements of I and $I_0$. The results are listed in Table 3

TABLE 3

| $[Cu^{2+}] + [Fe^{3+}]$ | $Cu^{2+}$ only | $Fe^{3+}$ only | $\Delta F(Cu^{2+} + Fe^{3+})$ Mixture | $\Delta F Cu^{2+} + \Delta F Fe^{3+}$ Sum |
|---|---|---|---|---|
| 0.2 mM + 0.2 mM | 0.03 | 0.08 | 0.11 | 0.11 |
| 0.5 mM + 0.2 mM | 0.06 | 0.16 | 0.2 | 0.22 |
| 1.0 mM + 1.0 mM | 0.12 | 0.26 | 0.37 | 0.38 |
| 0.5 mM + 1.0 mM | 0.06 | 0.26 | 0.33 | 0.32 |
| 1.0 mM + 0.5 mM | 0.12 | 0.16 | 0.25 | 0.28 |
| 1.0 mM + 0.05 mM | 0.14 | 0.04 | 0.17 | 0.18 |
| 1.0 mM + 0.1 mM | 0.14 | 0.08 | 0.20 | 0.22 |
| 1.0 mM + 0.2 mM | 0.14 | 0.12 | 0.25 | 0.26 |
| 1.0 mM + 0.5 mM | 0.14 | 0.24 | 0.34 | 0.38 |
| 0.05 mM + 1.0 mM | 0.02 | 0.37 | 0.40 | 0.39 |
| 0.1 mM + 1.0 mM | 0.03 | 0.37 | 0.42 | 0.40 |
| 0.2 mM + 1.0 mM | 0.05 | 0.37 | 0.44 | 0.42 |
| 0.5 mM + 1.0 mM | 0.09 | 0.37 | 0.48 | 0.46 |

Analysis of the results listed in Table 3 indicate that the presence of more than one metal in solution does not preclude the expected response of the fluorescent polymer composition to the second or even a third metal ion. This result is important in the simultaneous measurement of multi-component metal mixtures. Furthermore, the presence of two metals simultaneously in an aqueous mixture resulted in a near quantitative additivity of the individual $\Delta F$ values. For example, the poly(p-cresol-co-fluorescein) polymer was used to measure the $\Delta F$ values for several mixtures of $Cu^{2+}$ and $Fe^{3+}$. The results displayed in Table 3 indicate that for all $Cu^{2+}$ and $Fe^{3+}$ mixture concentrations employed, the overall $\Delta F$ values were the sum of the individual $\Delta F$ values, within experimental error.

Example 9

Fluorescence Changes of Polyphenol-based Compositions in the Presence of High NaCl Brines The fluorescent intensity and MEW of poly(p-cresol-co-fluorescein) to $Cu^{2+}$ was measured in a 0.5M NaCl solution. The calculated fluorescence response, $\Delta F$, was within experimental error of the values listed in Table 2 for poly(p-cresol-co-fluorescein).

Example 10

Fluorescence Changes of Fluorescent Polymer Compositions

The selectivity of the fluorophore-containing polymers for different metal ions can be used to generate a series of histograms illustrating a pattern of responses. The fluorescence responses are organized into statistical deviations around a mean response. The statistical analysis was calculated according to the equation: $\Delta Z=(\Delta F-x)/y$ where x and y represent the average deviation and standard deviation of each $\Delta F$ value, respectively, over a given metal ion data set. The statistical deviation ($\Delta Z$) for $Cu^{2+}$, $Fe^{2+}$, $Zn^{2+}$, $Mn^{2+}$ and $Fe^{3+}$ (each at 1 mM concentration) are shown in FIGS. 2–6. It can be seen from the figures that the pattern responses for each individual metal ion are unique. These histograms represent a fingerprint pattern for each metal ion that can be used to distinguish the metal in a solution and its concentration.

Example 11

Preparation of a 2-Dimensional Array of Polyphenol Containing Bound Fluorophores An array of homo- and copolymers of fluorescent polymers comprising a variety of different structures was prepared. The fluorescent polymer compositions are synthesized in an 8×8 array in a 96-well plate. Each well in the plate contains a specific ratio of phenols A and phenols B (phenols B can be fluorophore or phenol monomers) that are copolymerized as described in Example 2 to provide a series of copolymers. The series of copolymer are polymerized with a third set of monomers (either phenols or fluorophores). The polymerization steps described above are repeated to provide a wide variety of fluorescent polymer compositions with one or more in each of the 96 wells. A portion of a solution containing an analyte such as $Cu^{2+}$ and/or $Zn^{2+}$ metal ion(s) are added to each well and the fluorescence properties are determined as a function of the metals present in the solution and their concentrations. This procedure is repeated until a sufficient number of fluorescent responses is generated to provide a set of fluorescent patterns that is used to identify the different metal ions from each other and their concentrations.

It is not intended to limit the scope of the present invention to any theory or mechanism set forth herein to explain one or more results of the present invention. All publication, patents, and patent applications cited in this specification are herein incorporated by reference as if each individual publication, patent, or patent application were specifically and individually indicated to be incorporated by reference and set forth in its entirety herein. Moreover, U.S. Provisional Patent Application No. 60/095,111, filed on Aug. 3, 1998 is specifically hereby incorporated by reference in its entirety.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for sensing a number of analytes in solution, comprising:
    a sensor array including a plurality of different polymers, said polymers each including a plurality of phenolic repeating units and each having one of a plurality of different fluorescence responses to the analytes in solution;
    an excitation system operable to cause said polymers to fluoresce; and
    an emission detection system operable to detect said different fluorescence responses of each of said polymers to determine presence of the analytes when the probe is placed in the solution and said excitation system causes to polymers to fluoresce.

2. The apparatus of claim 1, further comprising a signal processor operatively coupled to said emission detection system, said signal processor being operable to generate:
   a detection pattern of signals from said different fluorescence responses;
   at least one comparison signal representing a comparison of the detection pattern to a number of identification patterns stored in said processor; and
   an output signal from said at least one comparison signal, said output signal representing at least one of the analytes.

3. The apparatus of claim 2, further comprising an output device responsive to said output signal to provide an indication of the presence of the at least one the analytes.

4. The apparatus of claim 1, wherein said array is operatively coupled to said excitation system and said detection system by a number of optic fibers.

5. The apparatus of claim 1, wherein a first one of said polymers only consists of said phenolic units and a second one of said polymers includes one or more first fluorophore units different from said phenolic units.

6. The apparatus of claim 5, wherein a third one of said polymers includes one or more second fluorophore units different from said one or more first fluorophore units.

7. The apparatus of claim 5, wherein said one or more first fluorophore units corresponds to a fluorophore having a free phenolic functionality or a free amino functionality.

8. The apparatus of claim 1, wherein at least one of said polymers includes at least one fluorophore unit different from said phenolic units.

9. The apparatus of claim 1 wherein at least one of the plurality of phenolic repeating units is a fluorophore unit.

10. An apparatus for sensing a number of analytes in solution, comprising:
   a sensor array comprising a plurality of different polymers, each of said polymers including a plurality of phenolic repeating units and at least one fluorophore unit and each of said polymers having one of a plurality of different fluorescence responses to the analytes in solution;
   an excitation system operable to cause said polymers to fluoresce; and
   an emission detection system operable to detect said different fluorescence responses of each of said polymers to determine presence of the analytes when the probe is placed in the solution and said excitation system causes to polymers to fluoresce.

11. The apparatus of claim 10, wherein the phenolic repeating unit is the same as the fluorophore unit.

12. The apparatus of claim 10, wherein the phenolic repeating unit is different from the fluorophore unit.

13. The apparatus of claim 10, further comprising a signal processor operatively coupled to said emission detection system, said signal processor being operable to generate:
   a detection pattern of signals from said different fluorescence responses;
   at least one comparison signal representing a comparison of the detection pattern to a number of identification patterns stored in said processor; and
   an output signal from said at least one comparison signal, said output signal representing at least one of the analytes.

14. The apparatus of claim 13, further comprising an output device responsive to said output signal to provide an indication of the presence of the at least one the analytes.

15. The apparatus of claim 10, wherein said array is operatively coupled to said excitation system and said detection system by a number of optic fibers.

16. The apparatus of claim 10, wherein a first one of said polymers only consists of said phenolic units and a second one of said polymers includes one or more first fluorophore units different from said phenolic units.

17. The apparatus of claim 16, wherein a third one of said polymers includes one or more second fluorophore units different from said one or more first fluorophore units.

18. The apparatus of claim 16, wherein said one or more first fluorophore units corresponds to a fluorophore having a free phenolic functionality or a free amino functionality.

19. The apparatus of claim 10, wherein at least one of said polymers includes at least one fluorophore unit different from said phenolic units.

20. A method for sensing analytes in solution, said method comprising:
   placing a first sensor array in contact with a solution comprising analytes, said first sensor comprising a plurality of different polymers, said polymers each including a plurality of phenolic repeating units and each polymer having one of a plurality of different fluorescence responses to the analytes in solution;
   causing one or more of said polymers to fluoresce; and
   detecting said different fluorescence responses of each of said polymers to determine the presence of the analytes.

* * * * *